(12) United States Patent
Hawkes

(10) Patent No.: US 9,232,965 B2
(45) Date of Patent: Jan. 12, 2016

(54) PRESS-ON LINK FOR SURGICAL SCREWS

(75) Inventor: David T. Hawkes, Pleasant Grove, UT (US)

(73) Assignee: Nexus Spine, LLC, Salt Lake City, UT (US)

(*) Notice: Subject to any disclaimer, the term of this patent is extended or adjusted under 35 U.S.C. 154(b) by 360 days.

(21) Appl. No.: 12/711,131

(22) Filed: Feb. 23, 2010

(65) Prior Publication Data

US 2010/0217334 A1    Aug. 26, 2010

Related U.S. Application Data

(60) Provisional application No. 61/154,511, filed on Feb. 23, 2009.

(51) Int. Cl.
*A61B 17/70* (2006.01)

(52) U.S. Cl.
CPC ......... *A61B 17/7007* (2013.01); *A61B 17/7013* (2013.01); *A61B 17/7014* (2013.01); *Y10T 29/49863* (2015.01)

(58) Field of Classification Search
CPC ........... A61B 17/7008; A61B 17/7011; A61B 17/7013; A61B 17/7014; A61B 17/7019; A61B 17/7049; A61B 17/705; A61B 17/7007; A61B 17/7023; A61B 17/7025
USPC ......... 606/250–253, 255–262, 264–266, 270, 606/278–279, 305–308, 328
See application file for complete search history.

(56) References Cited

U.S. PATENT DOCUMENTS 3,945,053 A    3/1976   Hillberry et al.
5,405,408 A    4/1995   Pitkin
(Continued)

FOREIGN PATENT DOCUMENTS

EP    1072228    1/2001
EP    1224915    7/2002
(Continued)

OTHER PUBLICATIONS

Jeanneau et al.; "A Complaint Rolling Contact Joint and it's Application in a 3-DOF Planar Parallel Mechanism with Kinematic Analysis"; Proceedings of DETC'04, ASME 2004 Design Engineering Technical Conferences and Computers and Information in Engineering Conference; Sep. 28-Oct. 2, 2004; Salt Lake City, Utah USA. DETC2004-57264, 2004by ASME.

(Continued)

*Primary Examiner* — Eduardo C Robert
*Assistant Examiner* — Julianna N Harvey
(74) *Attorney, Agent, or Firm* — Adam D. Stevens; Kirton McConkie

(57) ABSTRACT

A coupling assembly that is configured to couple a surgical screw to another coupling assembly and another surgical screw is disclosed. The coupling assembly comprises a body that includes a receptacle configured to receive a head portion of the surgical screw and hold the head portion through an interference fit. The body further includes either a female member, a male member, or both, the female member and the male member configured to mate with a female member and a male member of the another coupling assembly and thereby join the coupling assembly to the another coupling assembly. Embodiments of the coupling assembly provide for adjustment of the distance between the coupling assemblies, as well as misalignment of various axes of the coupling assembly relative to the surgical screw and the male member. Exemplary embodiments provide fewer parts, greater flexibility during the surgical implantation, and a smaller profile than previous coupling mechanisms.

10 Claims, 12 Drawing Sheets

(56) References Cited

U.S. PATENT DOCUMENTS

| | | |
|---|---|---|
| 5,415,661 A | 5/1995 | Holmes |
| 5,733,285 A | 3/1998 | Errico |
| 5,772,661 A | 6/1998 | Michelson |
| 5,964,760 A | 10/1999 | Richelsoph |
| 6,045,552 A | 4/2000 | Zucherman et al. |
| 6,063,089 A | 5/2000 | Errico et al. |
| 6,355,040 B1 | 3/2002 | Richelsoph |
| 6,379,354 B1 | 4/2002 | Rogozinski |
| 6,440,169 B1 | 8/2002 | Elberg et al. |
| 6,527,804 B1 | 3/2003 | Gauchet et al. |
| 6,540,785 B1 | 4/2003 | Gill et al. |
| 6,572,653 B1 | 6/2003 | Simonson |
| 6,579,320 B1 | 6/2003 | Gauchet et al. |
| 6,610,093 B1 | 8/2003 | Pisharodi |
| 6,626,904 B1 | 9/2003 | Jammet et al. |
| 6,645,248 B2 | 11/2003 | Casutt |
| 6,723,127 B2 | 4/2004 | Ralph et al. |
| 6,793,678 B2 | 9/2004 | Hawkins |
| 6,802,867 B2 | 10/2004 | Manasas et al. |
| 6,811,567 B2 | 11/2004 | Reiley |
| 6,863,688 B2 | 3/2005 | Ralph et al. |
| 6,936,071 B1 | 8/2005 | Marnay et al. |
| 6,949,123 B2 | 9/2005 | Reiley |
| 6,964,666 B2 | 11/2005 | Jackson |
| 6,966,910 B2 | 11/2005 | Ritland |
| 6,974,478 B2 | 12/2005 | Reiley et al. |
| 6,983,924 B2 | 1/2006 | Howell et al. |
| 6,991,632 B2 | 1/2006 | Ritland |
| 6,997,955 B2 | 2/2006 | Zubok et al. |
| 7,029,475 B2 | 4/2006 | Panjabi |
| 7,074,238 B2 | 7/2006 | Stinson et al. |
| 7,093,827 B2 | 8/2006 | Culpepper |
| 7,115,129 B2 | 10/2006 | Heggeness |
| 7,144,369 B2 | 12/2006 | Bardy |
| 7,144,396 B2 | 12/2006 | Shluzas |
| 7,207,992 B2 | 4/2007 | Ritland |
| 7,229,441 B2 | 6/2007 | Trieu et al. |
| 7,322,982 B2 | 1/2008 | Vincent-Prestigiacomo |
| 7,326,210 B2 | 2/2008 | Jahng et al. |
| 7,338,398 B2 | 3/2008 | Whiting et al. |
| 7,361,196 B2 | 4/2008 | Fallin et al. |
| 7,371,238 B2 | 5/2008 | Soboleski et al. |
| 7,377,942 B2 | 5/2008 | Berry |
| 7,445,635 B2 | 11/2008 | Fallin et al. |
| 7,458,981 B2 | 12/2008 | Fielding et al. |
| 7,476,238 B2 | 1/2009 | Panjabi |
| 7,476,251 B2 | 1/2009 | Zucherman et al. |
| 7,481,830 B2 | 1/2009 | Wall et al. |
| 7,485,133 B2 | 2/2009 | Cannon et al. |
| 7,485,134 B2 | 2/2009 | Simonson |
| 7,485,146 B1 | 2/2009 | Crook et al. |
| 7,491,218 B2 | 2/2009 | Landry et al. |
| 7,491,238 B2 | 2/2009 | Arnin et al. |
| 7,491,240 B1 | 2/2009 | Carver et al. |
| 7,494,507 B2 | 2/2009 | Dixon et al. |
| 7,537,615 B2 | 5/2009 | Lemaire |
| 7,618,441 B2 | 11/2009 | Groiso |
| 7,632,292 B2 | 12/2009 | Sengupta et al. |
| 7,909,877 B2 | 3/2011 | Krueger et al. |
| 8,025,681 B2 * | 9/2011 | Colleran et al. ............ 606/257 |
| 2002/0138077 A1 * | 9/2002 | Ferree ............................. 606/61 |
| 2002/0151900 A1 * | 10/2002 | Glascott ......................... 606/73 |
| 2003/0153912 A1 * | 8/2003 | Graf ................................ 606/61 |
| 2003/0171751 A1 | 9/2003 | Ritland |
| 2004/0002708 A1 | 1/2004 | Ritland |
| 2004/0176849 A1 | 9/2004 | Zubok et al. |
| 2005/0038432 A1 * | 2/2005 | Shaolian et al. ............... 606/61 |
| 2005/0101954 A1 | 5/2005 | Simonson |
| 2005/0113924 A1 | 5/2005 | Buttermann |
| 2005/0113927 A1 * | 5/2005 | Malek ............................ 606/61 |
| 2005/0125065 A1 | 6/2005 | Zucherman et al. |
| 2005/0149023 A1 | 7/2005 | Ritland |
| 2005/0159818 A1 | 7/2005 | Blain |
| 2005/0165487 A1 | 7/2005 | Muhanna et al. |
| 2005/0177156 A1 * | 8/2005 | Timm et al. .................... 606/61 |
| 2005/0192573 A1 | 9/2005 | Abdelgany et al. |
| 2005/0203516 A1 | 9/2005 | Biedermann et al. |
| 2005/0228382 A1 | 10/2005 | Richelsoph et al. |
| 2005/0240270 A1 | 10/2005 | Zubok et al. |
| 2005/0261772 A1 | 11/2005 | Filippi et al. |
| 2005/0277932 A1 * | 12/2005 | Farris ............................. 606/61 |
| 2006/0009766 A1 * | 1/2006 | Lee et al. ....................... 606/61 |
| 2006/0009768 A1 | 1/2006 | Ritland |
| 2006/0009850 A1 | 1/2006 | Frigg et al. |
| 2006/0025770 A1 | 2/2006 | Schlapfer et al. |
| 2006/0036240 A1 | 2/2006 | Colleran et al. |
| 2006/0041314 A1 | 2/2006 | Millard |
| 2006/0052784 A1 | 3/2006 | Dant et al. |
| 2006/0084987 A1 * | 4/2006 | Kim ................................ 606/61 |
| 2006/0189983 A1 | 8/2006 | Fallin et al. |
| 2006/0190079 A1 | 8/2006 | Istephanous et al. |
| 2006/0217712 A1 | 9/2006 | Mueller et al. |
| 2006/0229609 A1 * | 10/2006 | Wang ............................. 606/61 |
| 2006/0240533 A1 | 10/2006 | Sengupta et al. |
| 2006/0271047 A1 | 11/2006 | Jackson |
| 2006/0271051 A1 | 11/2006 | Berrevoets et al. |
| 2007/0016193 A1 | 1/2007 | Ritland |
| 2007/0028714 A1 | 2/2007 | Lusk et al. |
| 2007/0043365 A1 | 2/2007 | Ritland |
| 2007/0049936 A1 | 3/2007 | Colleran et al. |
| 2007/0088440 A1 | 4/2007 | Eisermann et al. |
| 2007/0179618 A1 | 8/2007 | Trieu et al. |
| 2007/0270814 A1 * | 11/2007 | Lim et al. ...................... 606/61 |
| 2008/0015588 A1 | 1/2008 | Hawkes |
| 2008/0027436 A1 * | 1/2008 | Cournoyer et al. ............ 606/61 |
| 2008/0071273 A1 * | 3/2008 | Hawkes et al. ................ 606/61 |
| 2008/0077246 A1 | 3/2008 | Fehling et al. |
| 2008/0140075 A1 | 6/2008 | Ensign et al. |
| 2008/0154308 A1 | 6/2008 | Sherman et al. |
| 2008/0167688 A1 | 7/2008 | Fauth et al. |
| 2008/0183209 A1 | 7/2008 | Robinson et al. |
| 2008/0195208 A1 | 8/2008 | Castellvi |
| 2008/0195213 A1 | 8/2008 | Halverson et al. |
| 2008/0234739 A1 | 9/2008 | Hudgins et al. |
| 2008/0312693 A1 | 12/2008 | Trautwein et al. |
| 2009/0005819 A1 | 1/2009 | Ben-Mokhtar et al. |
| 2009/0048631 A1 | 2/2009 | Bhatnagar et al. |
| 2009/0171392 A1 * | 7/2009 | Garcia-Bengochea et al. ............................ 606/246 |
| 2009/0228045 A1 | 9/2009 | Hayes et al. |
| 2009/0259257 A1 | 10/2009 | Prevost |
| 2009/0270921 A1 | 10/2009 | Krause |
| 2010/0204732 A1 | 8/2010 | Aschmann et al. |
| 2010/0211106 A1 | 8/2010 | Bowden et al. |
| 2010/0217324 A1 | 8/2010 | Bowden et al. |
| 2010/0217326 A1 | 8/2010 | Bowden et al. |
| 2010/0222821 A1 | 9/2010 | Bowden et al. |
| 2010/0222823 A1 | 9/2010 | Bowden et al. |
| 2010/0241232 A1 | 9/2010 | Halverson et al. |

FOREIGN PATENT DOCUMENTS

| | | |
|---|---|---|
| EP | 1970031 | 9/2008 |
| KR | 1020050080493 | 8/2005 |
| KR | 1020060113318 | 11/2006 |
| WO | WO 2004/071344 | 8/2004 |
| WO | WO 2005/051243 | 6/2005 |
| WO | WO 2005/107654 | 11/2005 |
| WO | WO 2006127992 | 11/2006 |
| WO | WO 2007/041265 | 4/2007 |
| WO | WO 2008/070840 | 6/2008 |
| WO | WO 2008/100891 | 8/2008 |
| WO | WO 2010/030906 | 3/2010 |
| WO | WO 2010/096621 | 8/2010 |
| WO | WO 2010/096829 | 8/2010 |
| WO | WO 2010/108010 | 9/2010 |

OTHER PUBLICATIONS

Cannon et al.; "Complaint Rolling-Contact Element Mechanisms"; Proceedings of IDETC/CIE 2005, 2005 ASME Design Engineering Technical Conferences & Computers and Information in Engineering Conference, Sep. 24-28, 2005, 2005; Long Beach, California, USA; DETC2005-84073.

(56) References Cited

OTHER PUBLICATIONS

Halverson et al.; "Concepts for Achieving Multi-Stability in Complaint Rolling-Contact Elements"; Proceedings of IDETC/CIE 2007; ASME 2007 International Design Engineering Technical Conferences & Computers and Information in Engineering Conference; Sep. 24-28, 2007; Las Vegas, USA; DETC2007-34836.

Halverson et al.; Tension-Based Multi-Stable Complaint Rolling-Contact Elements: 13th National Conference on Mechanisms and Machines (NaCoMM-2007); IISc, Bangalore, India; Dec. 12-13, 2007.

Jacobsen et al.; "Components for the design of Lamina Emergent Mechanism"; Proceedings of IMECE 2007, 2007 ASME International Mechanical Engineering Congress and Exposition; Nov. 10-16, 2007; Seattle, USA.

Jacobsen et al.; "Mechanism and Machine Theory"; Mechanism and Machine Theory; 2009; pp. 2098-2109; vol. 44; Elsevier.

Stratton et al.; Force-Displacement Model of the Flexsure™ Spinal Implant; Proceedings of the ASME 2010 International Design Engineering Technical Conferences and Computers and Information in Engineering Conference IDETC/CIE; Aug. 15-18, 2010; Montreal, Quebec, Canada.

U.S. Appl. No. 12/916,110, filed Oct. 29, 2010; Spencer P. Magleby.

U.S. Appl. No. 11/952,709, filed Dec. 7, 2007; Michael D. Ensign; office action received Sep. 24, 2010.

PCT Application PCT/US2010/025101; filing date Feb. 23, 2010; David Hawkes; ISR mailed Sep. 27, 2010.

PCT Application PCT/US2007/086803; filing date Dec. 7, 2007; Michael D. Ensign; ISR mailed May 19, 2008.

PCT Application PCT/US2008/053661; filing date Feb. 12, 2008; Peter Halverson; ISR mailed Jun. 5, 2008.

PCT Application PCT/US2010/024674; filing date Feb. 19, 2010; Anton E. Bowden; ISR mailed Nov. 19, 2010.

PCT Application PCT/US2010/027826; filing date Mar. 18, 2010; Peter A. Halverson; ISR mailed Jan. 17, 2011.

U.S. Appl. No. 12/709,240, filed Feb. 19, 2010; Anton E. Bowden; office action issued Dec. 30, 2011.

U.S. Appl. No. 11/952,709, filed Dec. 7, 2007; Michael D. Ensign; office action mailed Mar. 17, 2011.

U.S. Appl. No. 12/709,240, filed Feb. 19, 2010; Anton E. Bowden; office action issued Aug. 29, 2011.

U.S. Appl. No. 12/709,243, filed Feb. 19, 2010; Anton E. Bowden; office action issued Sep. 1, 2011.

U.S. Appl. No. 12/709,248, filed Feb. 19, 2010; Anton E. Bowden; office action issued Sep. 13, 2011.

U.S. Appl. No. 12/709,255, filed Feb. 19, 2010; Anton E. Bowden; office action issued Sep. 15, 2011.

U.S. Appl. No. 12/029,046, filed Feb. 11, 2008; Peter Halverson; office action issued Sep. 22, 2011.

U.S. Appl. No. 12/709,246, filed Feb. 19, 2010; Anton E. Bowden; office action issued Sep. 1, 2011.

U.S. Appl. No. 12/709,240, filed Feb. 19, 2010; Anton E. Bowden; office action dated Jul. 11, 2012.

U.S. Appl. No. 12/916,110, filed Oct. 29, 2010; Spencer P. Magleby; office action issued Mar. 16, 2012.

U.S. Appl. No. 120/029,046, filed Feb. 11, 2008; Peter Halverson; office action issued Apr. 20, 2012.

U.S. Appl. No. 12/709,240, filed Feb. 19, 2010; Anton E. Bowden; office action dated Apr. 22, 2013.

U.S. Appl. No. 11/952,709, filed Dec. 7, 2007; Michael D. Ensign; office action dated Nov. 6, 2013.

U.S. Appl. No. 11/284,438, filed Nov. 21, 2005; Michael D. Ensign; office action dated Nov. 12, 2013.

U.S. Appl. No. 12/726,816, filed Mar. 18, 2010; Peter Halverson; office action issued Jan. 31, 2013.

PCT Application PCT/US2012/041360; filing date Jun. 7, 2012; Eric Dodgen; International Search Report mailed Dec. 14, 2012.

U.S. Appl. No. 12/916,110, filed Oct. 29, 2010; Spencer P. Magleby; office action issued Dec. 14, 2012.

PCT Application PCT/US2013/066292; filing date Oct. 23, 2013; Nexus Spine, L.L.C.; international search report mailed Jan. 22, 2014.

\* cited by examiner

PRESS-ON LINK FOR SURGICAL SCREWS

PRIORITY CLAIM

This application claims the benefit of and priority from U.S. Provisional Patent Application No. 61/154,511 filed on Feb. 23, 2009 that is incorporated in its entirety for all purposes by this reference.

FIELD

Embodiments of the present invention relate generally to coupling mechanisms for surgical implants and, more particularly, coupling mechanism for use with various orthopedic rod placement devices.

BACKGROUND

The use of bone stabilization/fixation devices to align or position bones is well established. Furthermore, the use of spinal bone stabilization/fixation devices to align or position specific vertebrae or a region of the spine is well established. Typically such devices use a coupling assembly to connect or link two or more surgical screws and/or pedicle screws together to stabilize the bone and/or joint around which the screws are fixed. The coupling assembly typically is comprised of a relatively rigid member such as a plate or a rod that is used to couple or join adjacent structures or parts of the anatomy. Once the coupled structures are spatially fixed in position, procedures can be completed, healing can proceed, and the like.

Conventional surgical and/or pedicle screw coupling systems, however, have several drawbacks. Those coupling systems are rather large and bulky, which can result in more tissue damage in and around the surgical site, both from when the coupling system is installed during surgery and from implant induced, post-operative tissue irritation and erosion. The relative bulk of the prior art devices may be particularly relevant in supra-fascial applications. The prior art coupling systems have a rod-receiving device that is delivered to the surgeon already coupled or attached to the head of the surgical screw, which poses two challenges: 1) this prevents certain surgical maneuvers (e.g. placing the screws prior to interbody work); and, 2) increases the carrying cost of the inventory. Furthermore, traditional coupling systems do not allow for varying the rod stiffness along a multi-segmented construct; certain indications may require a stiff rod over one segment and a flexible rod over another. Further, with traditional systems there is an inability to easily extend a fusion; that is to say that in a revision procedure the existing rod would need to be removed rather than just adding a short rod segment to the end of the coupling system. In addition, some of the prior art coupling systems include locking components (e.g., set screws and the like) that must all be carefully assembled together during the surgical procedure. Further, many traditional surgical screw system designs preclude the ability to be placed percutaneously over a guide wire, which makes these systems more difficult to install and maneuver during surgical procedures, including minimally invasive procedures.

Moreover, prior art devices require that the rod be assembled to the coupling device after the screw is inserted in the bone, which can be disadvantageous at times, whereas the option to assemble the rod to the coupling device outside the wound may prove valuable. Also, existing coupling systems necessitate simultaneous locking of all components, which prevents the ability to properly compress a coupling system along the rod because the angle relative to the surgical screw would change. Yet further still, to accommodate various anatomies and/or misplacement of surgical screws due to simple tolerance variances and/or error, requires a surgeon to bend the rod, thus further increasing cost and complexity. An example of such a prior art surgical screw system is disclosed in U.S. Pat. Publ. No. 2008/0140075, titled Press-On Pedicle Screw System, which has a common inventor with this application and is owned by the assignee of this application.

Thus, there exists a need for a coupling system for surgical screws that accommodates and allows for misalignment and/or varying tolerances and/or differing anatomies and/or geometries.

There also exists a need for a coupling system or assembly that is smaller in profile than existing coupling systems, which may be particularly applicable to supra-fascial placement.

There is a need for coupling systems better adapted for use over a guide wire, and with minimally invasive surgical techniques, such as endoscopy.

There also exists a need for a coupling system that comprises fewer components (e.g., no set screws), has a lower profile, and accommodates easier assembly and/or disassembly in-situ (i.e., within the patient) and before implantation than existing coupling systems. This includes the ability to assemble the rod to the coupling/connecting device prior to placement in the surgical wound.

There also exists a need for a coupling system that allows for varying the stiffness of the coupling system. For example, it may be appropriate to apply a rigid rod to a fused segment and a flexible member to an adjacent segment.

There is a need for a system that provides for simple extension of a coupling system in revision surgery.

There is a need to decrease the carrying cost of inventory by eliminating the requirement of placing a connecting-device on each pedicle screw prior to implantation.

There is a need to eliminate rod bending in multi-segment constructs.

SUMMARY

Various features and embodiments of the invention disclosed herein have been the subject of substantial ongoing experimentation and have shown a significant improvement over the prior art. Among other improvements, the embodiments of the invention provide robust and durable coupling assemblies that have a smaller profile with fewer components and greater ease of assembly with more surgical options than prior art devices. It is believed that the embodiments, collectively and/or individually, represent an unexpected advance in the field and will enable physicians to more easily adjust and/or accommodate for various factors.

Embodiments of the present invention include a coupling assembly that includes a first body. The first body includes an upper bore and a receptacle for receiving a head portion of a surgical screw. The receptacle is configured to provide an interference fit with the head portion, thereby retaining the body against the surgical screw. Embodiments of the body include one or more female member(s), a male member(s), or a combination of female and male members. The female member is configured to receive and to provide an interference fit to a male member of an another body proximate the first body, thereby linking or connecting the first body to another body. Embodiments of the male member include a spherical face that is configured to accommodate misalignment between a first axis of the body and a long axis of the male member. Likewise, embodiments of the body include a receptacle that is optionally configured to accommodate misalignment between a second axis of the body and a long axis of the surgical screw. Embodiments of the body optionally include a cannula connecting the female member to the upper bore that allows any fluids within the female member to escape through the upper bore when the male member is inserted or received within the female member.

Another embodiment of the coupling assembly includes a first body, an upper bore and a receptacle for receiving a head portion of a surgical screw. The coupling assembly optionally includes a split-ring assembly configured to receive said head portion of said surgical screw, rather than the previous embodiment which received the head portion of the surgical screw directly within the receptacle. The split-ring optionally includes a plurality of fingers separated from one another by a slot, the fingers configured to elastically engage the head portion of the surgical screw. In this embodiment, the receptacle then receives and provides an interference fit for the split ring assembly, holding the fingers against the head portion. Optionally, the split-ring assembly is separable from the receptacle and the first body. Embodiments of the body include one or more female member(s) that are configured to receive and to provide an interference fit to a male member of a coupling rod. Embodiments of the male members of the coupling rod, one male member being opposite from another male member along a long axis of the coupling rod, optionally includes a locking mechanism, such as a hex-end, threads, snap-locks, and other similar locking mechanisms. For example, an embodiment of the locking mechanism includes a first locking mechanism on the first male member, and a second locking mechanism on the second male member, the two locking mechanisms locking upon rotating the coupling rod in one direction. Embodiments of the male are configured to accommodate misalignment between a first axis of the body and a long axis of the coupling rod. Likewise, embodiments of the body include a receptacle and split-ring assembly that is optionally configured to accommodate misalignment between a second axis of the body and a long axis of the surgical screw. Embodiments of the body optionally include a cannula connecting the female member to the upper bore that allows any fluids within the female member to escape through the upper bore when the male member is inserted or received within the female member.

Methods of making and using embodiments of the coupling assemblies disclosed in the application are also provided.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

To further clarify the above and other advantages and features of the one or more present inventions, reference to specific embodiments thereof are illustrated in the appended drawings. The drawings depict only exemplary embodiments and are therefore not to be considered limiting. One or more embodiments will be described and explained with additional specificity and detail through the use of the accompanying drawings in which.

The drawings are not necessarily to scale.

DETAILED DESCRIPTION

Figure 1:
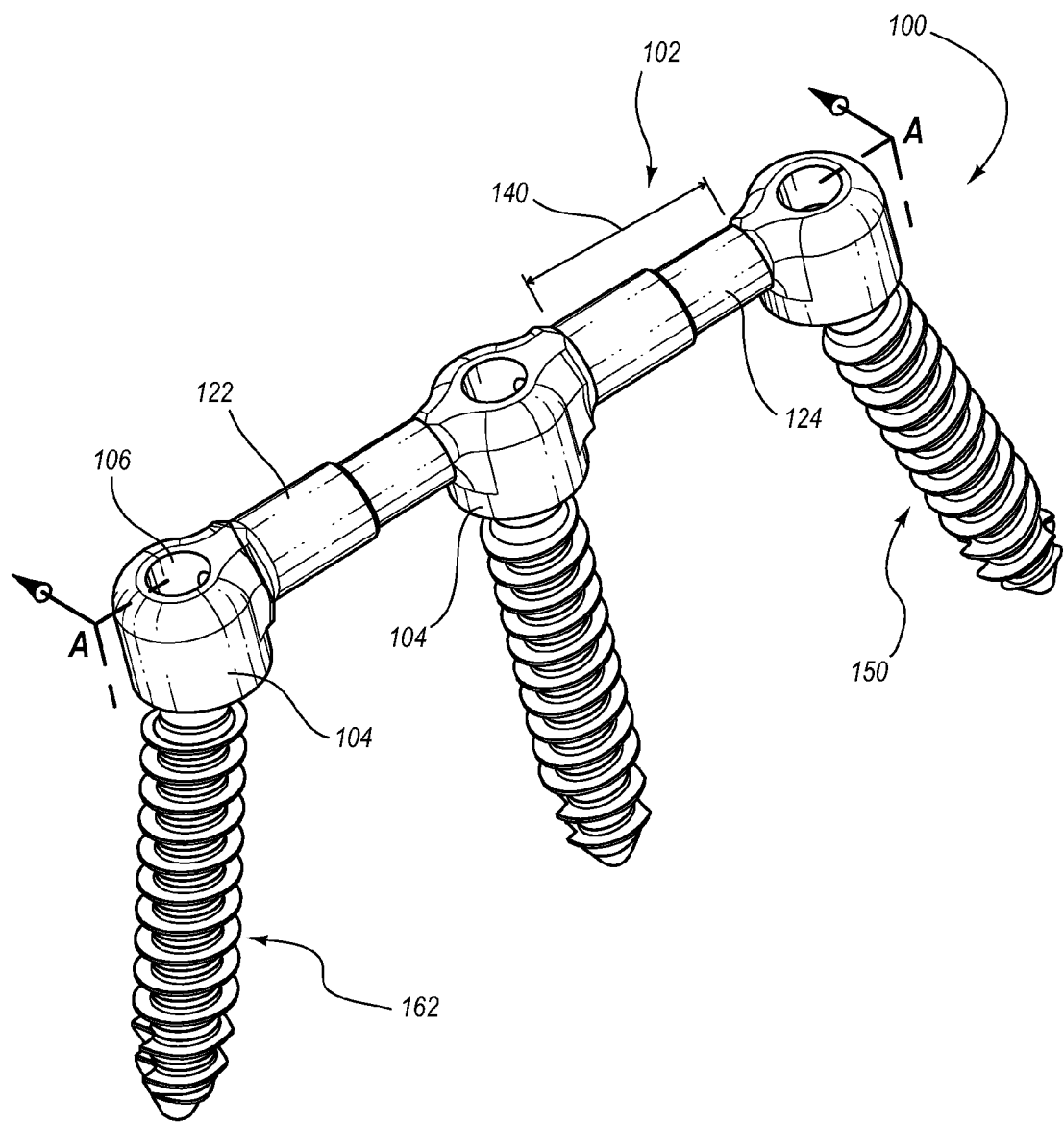
FIG. 1 is an embodiment of a coupling assembly coupled to surgical screws.
Figure 2:
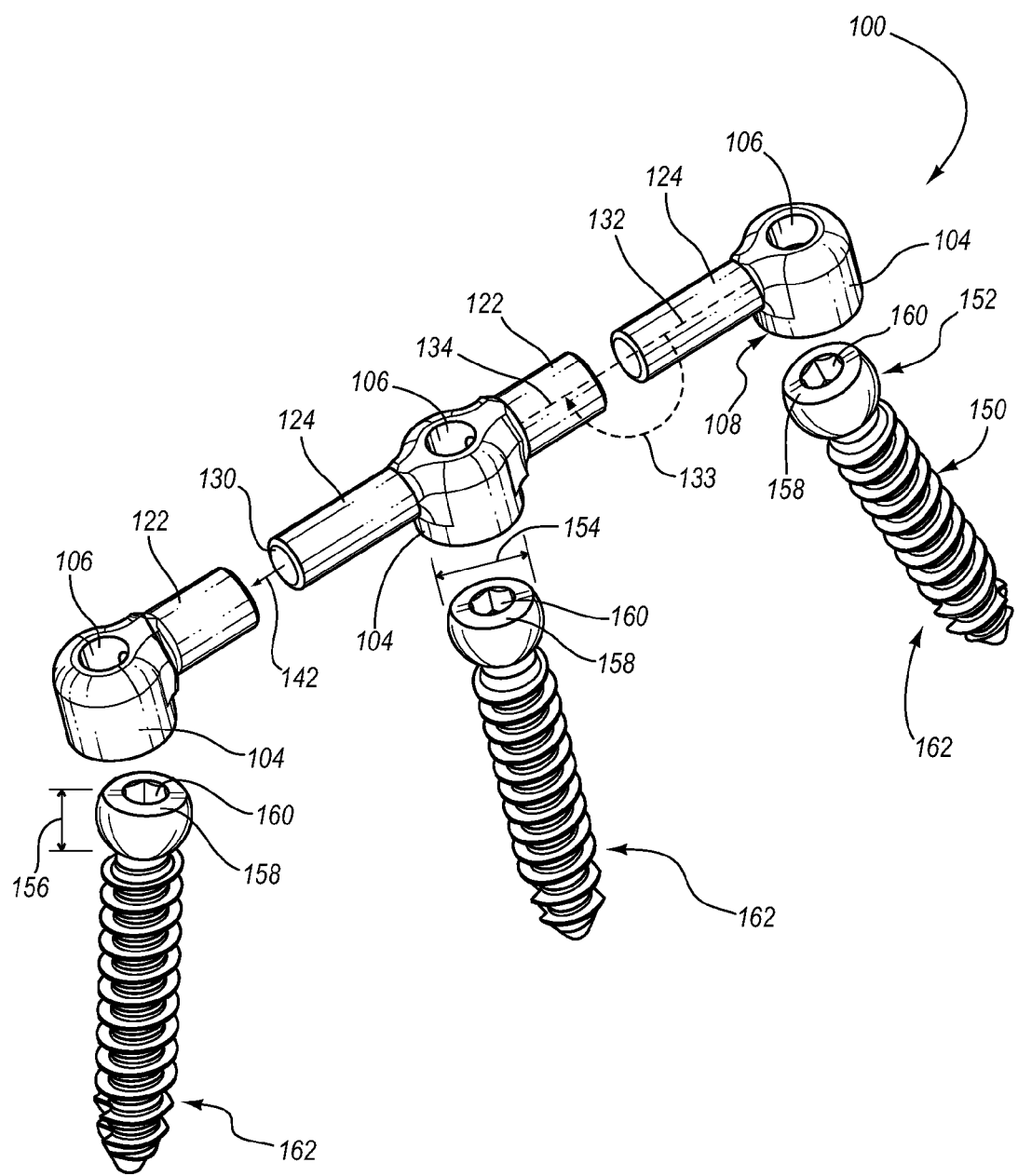
FIG. 2 is an exploded view of the embodiment of the coupling assembly shown in FIG. 1.
Figure 3:
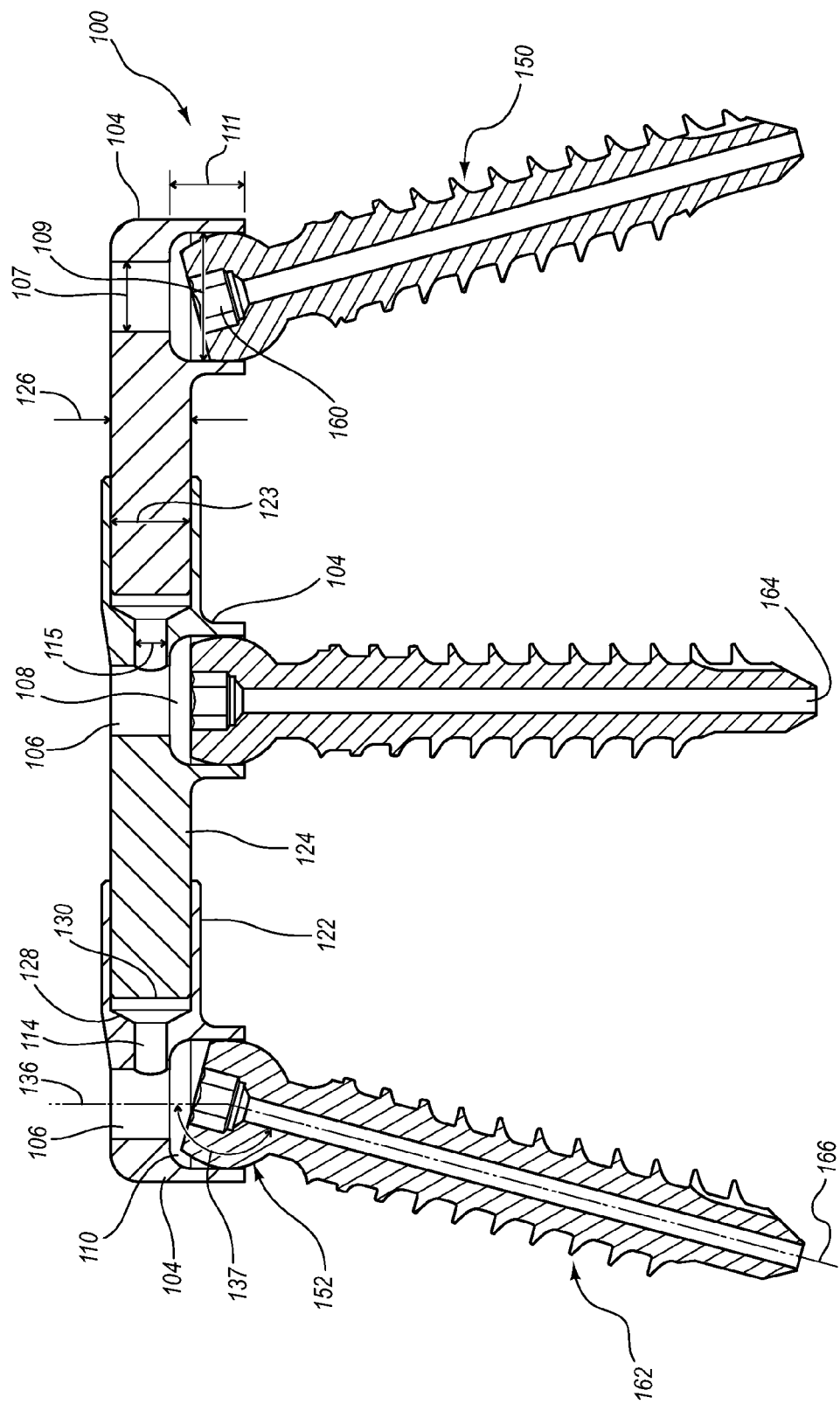
FIG. 3 is a view of cross-section A-A of the embodiment of the coupling assembly shown in FIG. 1.

Turning to FIGS. 1-3, a surgical screw system 100 that includes a plurality of various embodiments of coupling assemblies 102 disclosed herein are illustrated connecting three surgical screws 150 having a threaded portion 162 together. It will be understood that various embodiments of coupling system are capable of being used with a variety of orthopedic rod placement devices, hooks, and/or surgical screws, including, but not limited to, pedicle screws and orthopedic rods used in spinal surgery. The coupling assembly 100 is sometimes referred to as a yolk or tulip assembly, but for purposes of this disclosure the more generic term coupling assembly will be used.

The coupling assembly 102 includes at least one body 104; thus, an entire coupling assembly 102 may include a plurality of bodies 104, such as the three bodies 104 illustrated in FIG. 1. The body 104 is illustrated as having a cylindrical shape, although other shapes such as ovoid, spherical, square, and so forth fall within the scope of the disclosure. The body 104 includes an upper bore 106. The body 104 also optionally includes one or more female members 122, one or more male members 124, or a combination of female members 122 and male members 124. Thus, while FIG. 1 illustrates bodies 104 that have one or two male members 124 and/or female members 122, one having skill in the art would understand that a body 104 could have 3, 4, or more male members 124 and/or female members 122, depending on the intended purpose of the coupling assembly 102. The male member can be rigid, semi-rigid, or flexible, depending on the application.

Referring to FIG. 2, the embodiment of the surgical screw system 100 and the coupling assembly 102 of FIG. 1 is shown in exploded view. The surgical screws 150 include a threaded portion 162 configured to engage the bone of a patient as part of an orthopedic surgical procedure. The surgical screws 150 have a head portion 152 that is received by the coupling assembly 102 as will be discussed in further detail below. The head portion 152 has a height 156 and an outer diameter 154. The head portion 152 also includes a driving feature 160 for use with various tools to drive the surgical screw 150 into the bone. Illustrated in FIG. 2, the driving feature 160 is an Allen-key or hex-head configuration, although other configurations are known in the art, such as hex-a-lobe. The surgical screw 150 includes a screw long axis 166 and a screw cannula 164, illustrated in the cross-section A-A in FIG. 3. As one having skill in the art would understand, the screw cannula 164 allows the surgical screw to be maneuvered over and to receive a Kirschner wire (typically referred to as a K-wire; not illustrated), a type of guide wire used to aid in the precise placement of the surgical screw in the bone.

Referring back to FIG. 2, the male member 124 includes a long axis 132 that aligns, to a greater or lesser degree with a first axis 134 of the body. By align, it is meant that the long axis 132 and the first axis 134 will be approximately coincident when the male member 124 is inserted via a force 142 into the female member 122 of the body 104. As will be discussed in further detail below, it is often not practical and, sometimes, even possible, to have the long axis 132 and the first axis 134 be coincident due to the tolerances of the manufacturing and surgical placement process, simple variances in the anatomies between patients and other factors. Thus, there often exists a first angle 133 between the intersection of the long axis 132 and the first axis 134, for which the prior art could not easily accommodate or easily allow.

Referring now to FIG. 3, the body 104 optionally includes a cannula 114 having a cannula inner diameter (or height, if the cannula is not cylindrical) 115. The cannula 114 is connected to the upper bore 106 and provides a route for any fluids, such as blood, entrapped in the female member 122 to escape when the male member 124 is inserted into the female member 122.

The female member 122 has a female inner diameter (or height, if the female member 122 is not cylindrical) 123 and the male member 124 has an outer diameter (or height, if the male member 124 is not cylindrical) 126. The female member 122 is configured to receive and to provide an interference fit or press fit to the male member 124. The term interference fit shall be interpreted broadly as including the joining of any two mating parts such that one or the other (or both) parts slightly deviate in size from their nominal dimension, thereby deforming each part slightly, each being compressed, the interface between two parts creating a union of extremely high friction. The word interference refers to the fact that one part slightly interferes with the space that the other is occupying in its nominal dimension. Optionally, the interference fit can be configured to require at least 800 pounds of force to remove the male member 124 from the female member 122.

The female inner diameter 123 can be constant, or it can be sloped or have steps through the inner length of the female member 122 up until a shoulder 128 that prevents the male member 124 from advancing any further into the female member 122. Thus, the female inner diameter 123 may be larger than an interference fit diameter near a mouth of the female member 122, thereby allowing the male member 124 to rotate, pivot, enter, and exit freely or semi-freely within the female member 122. As the male member 124 is pressed further into the female member 122, the female inner diameter 123 optionally necks down, becoming smaller or narrower, either smoothly or in steps, until an interference fit is achieved. Thus, it will be understood that the female member 122 optionally provides, in part, the ability to adjust the distance 140 between bodies 104.

The shoulder 128 optionally narrows or necks down from the female inner diameter 123 to the cannula inner diameter 115, or it can optionally neck down in steps. The shoulder 128 optionally includes a lip or ridge that prevents a male face 130 of the male member 124 from advancing beyond the shoulder 128.

Still referring to FIG. 3, the body or bodies 104, as noted, include an upper bore 106 having a bore inner diameter (or width, if the upper bore 106 is not cylindrical) 107. As noted, the upper bore 106 is fluidly connected to the cannula 114. The upper bore 106 is also fluidly connected to the receptacle 108. The bore inner diameter 107 is less than the receptacle inner diameter (or width, if the receptacle 108 is not cylindrical) 109. Optionally, the bore inner diameter 107 is sufficiently wide to accommodate a K-wire or other guiding mechanism threaded through the screw cannula 164 as discussed above.

The receptacle 108, in addition to the receptacle inner diameter 109, has a height 111 and a shoulder, or screw head contact surface 110. As with the female member 122, the receptacle 108 is configured to receive a head portion 152 of the surgical screw 150 and to provide an interference or press fit between the receptacle 108 and the head portion 152. The receptacle inner diameter 109 can be constant, or it can be sloped or have steps though the inner height 111 of the receptacle 108 up until the screw head contact surface or shoulder 110 that prevents the head portion 152 from advancing any further into the receptacle 108. Thus, the receptacle inner diameter 109 may be larger than an interference fit diameter near a mouth of the receptacle 108, thereby allowing the head portion 152 to rotate, enter, and exit freely or semi-freely within the receptacle 108. As the head portion 152 is pressed further into the receptacle 108, the receptacle inner diameter 109 optionally necks down, becoming smaller or narrower, either smoothly or in steps, until an interference fit is achieved.

The body 104 and, hence, the receptacle 108 includes a second axis 136. The second axis 136 may align, to a greater or lesser degree with the screw long axis 166 of the surgical screw 150, as is the case for the middle body 104. By align, it is meant that the screw long axis 166 and the second axis 136 will be approximately coincident when the head portion 152 of the surgical screw 150 is inserted into the receptacle 108 of the body 104. As will be discussed in further detail below, it is often not practical and, sometimes, even possible, to have the screw long axis 166 and the second axis 136 be coincident due to the tolerances of the manufacturing and surgical placement process, simple variances in the anatomies between patients and other factors. In other circumstances, the screw long axis 166 intersects the second axis 136 of the body at a second angle 137, as illustrated in the left most body 104 of FIG. 3, for which the prior art could not easily accommodate or easily allow.

Figure 4:
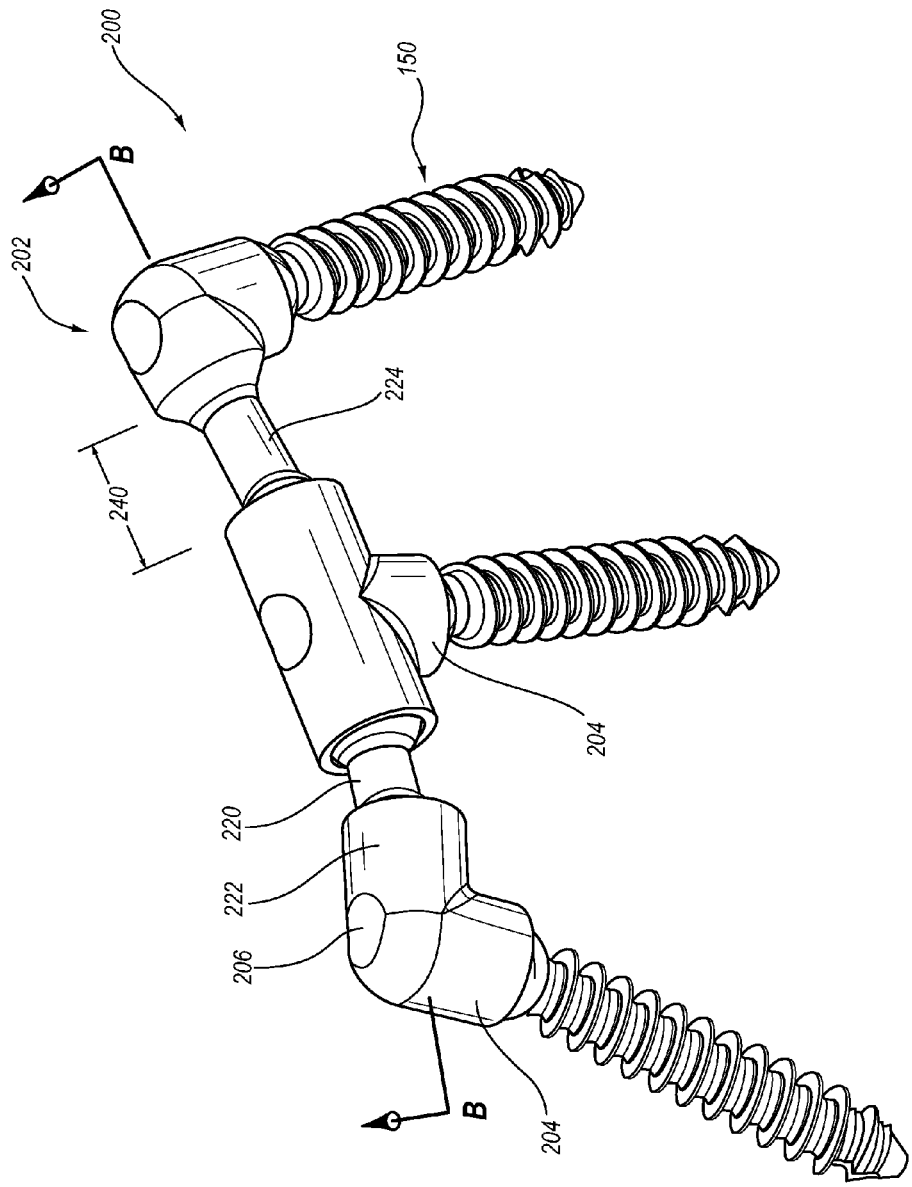
FIG. 4 is another embodiment of a coupling assembly coupled to surgical screws.
Figure 5:
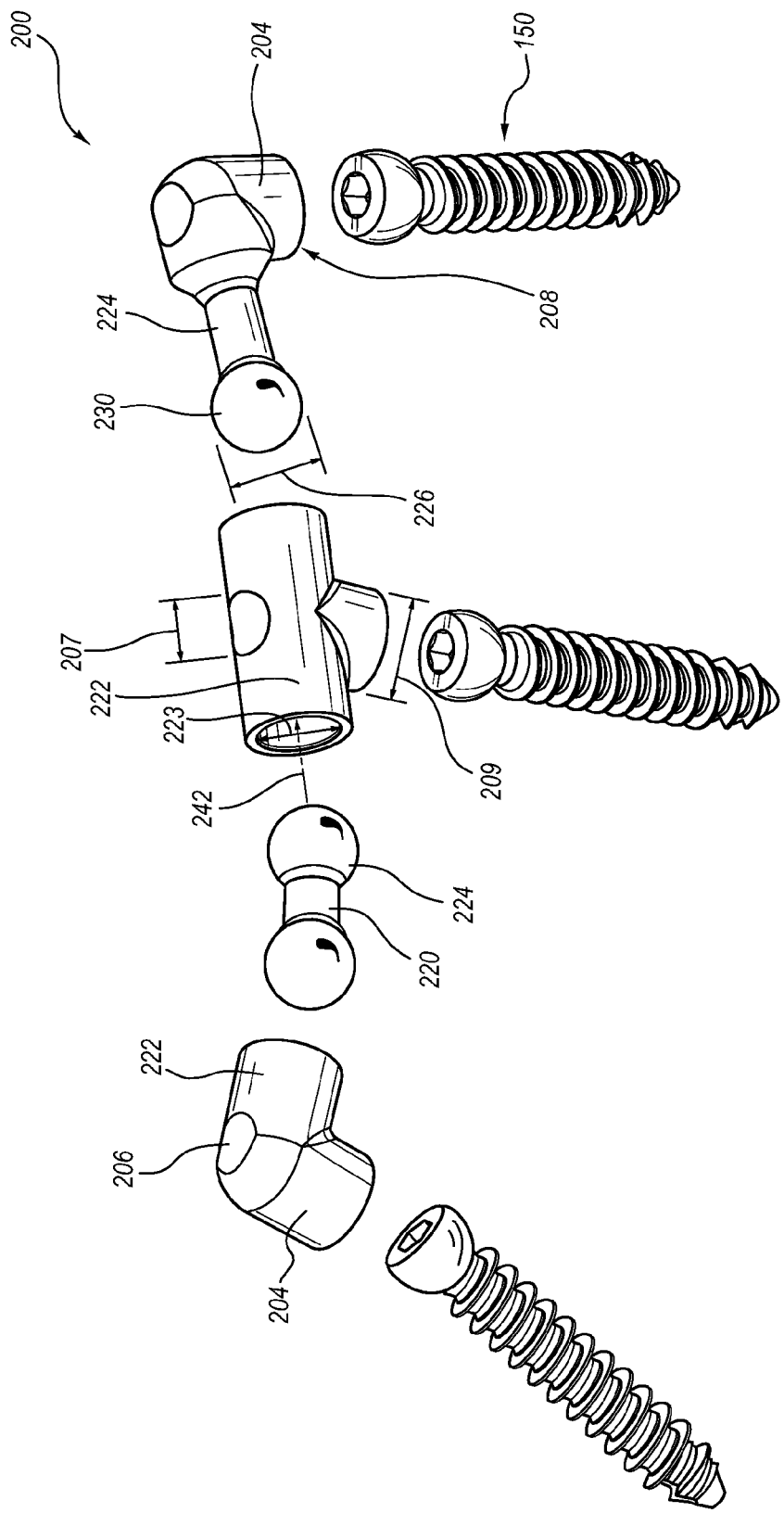
FIG. 5 is an exploded view of the embodiment of the coupling assembly shown in FIG. 4.
Figure 6:
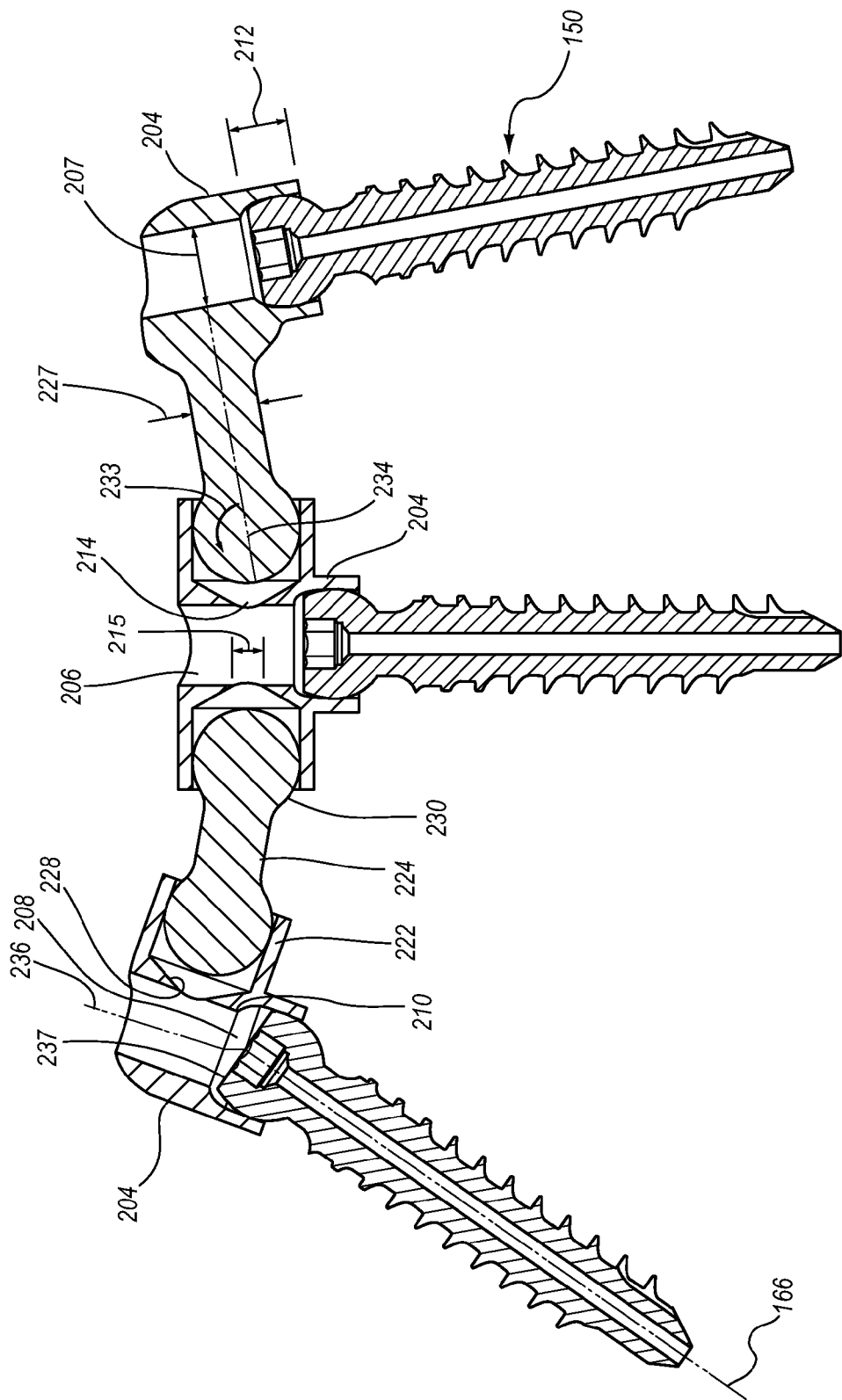
FIG. 6 is a view of cross-section B-B of the embodiment of the coupling assembly shown in FIG. 4.

Referring to FIGS. 4-6, another embodiment of a surgical screw system 200 that includes a plurality of another embodiment of coupling assemblies 202 disclosed herein are illustrated connecting three surgical screws 150 having a threaded portion 162 together. The surgical screws 150 illustrated were previously described above, thus reference should be made to that description.

The coupling assembly 202 includes at least one body 204; thus, an entire coupling assembly 202 may include a plurality of bodies 204, such as the three bodies 204 illustrated in FIG. 4. The body 204 is illustrated as having a cylindrical shape, although other shapes such as ovoid, spherical, square, and so forth fall within the scope of the disclosure. The body 204 includes an upper bore 206. The body 204 also optionally includes one or more female members 222, one or more male members 224, a combination of female members 222 and male members 224, and, optionally, a coupling rod 220 that includes two or more male members 224 or female members 222. (Illustrated are coupling rods 220 with male members 224, but this is just one embodiment of the coupling rod, as will be understood.) Thus, while FIG. 4 illustrates bodies 204 that have one or two male members 224 and/or female members 222, and one coupling rod 220, one having skill in the art would understand that a body 204 could have 3, 4, or more male members 224 and/or female members 222 and/or coupling rods 220, depending on the intended purpose of the coupling assembly 202.

Referring to FIG. 6, the embodiment of the surgical screw system 200 and the coupling assembly 202 of FIG. 1 is shown in cross-section B-B. The male member 224 and the coupling rod 220 include a long axis 232 (not illustrated on the coupling rod 220) that aligns, to a greater or lesser degree with a first axis 234 of the body. By align, it is meant that the long axis 232 and the first axis 234 will be approximately coincident when the male member 224 (whether included with a body 204 or a coupling rod 220) is inserted via a force 242 (FIG. 5) into the female member 222 of the body 204. As will be discussed in further detail below, it is often not practical and, sometime, even possible, to have the long axis 232 and the first axis 234 be coincident due to the tolerances of the manufacturing and surgical placement process, simple variances in the anatomies between patients and other factors. Thus, there often exists a first angle 233 between the intersection of the long axis 232 and the first axis 234, for which the prior art could not easily accommodate or easily allow. As seen in FIGS. 5 and 6, this embodiment optionally includes a male member 224 that has male face 230 that is a sphere in this instance, although other shapes and configurations, including ovoid, square, and the like, fall within the scope of the disclosure. An advantage of the male face 230 of spherical shape is that provides for a greater range of motion and possible angles 233 than may otherwise be accommodated, thus providing greater ease of use and accommodation for a wider variety of factors that a surgeon might encounter while connecting the coupling assembly to a surgical screw or screws.

Still referring to FIG. 6, the body 204 optionally includes a cannula 214 having a cannula inner diameter (or height, if the cannula is not cylindrical) 215. The cannula 214 is connected to the upper bore 206 and provides a route for any fluids, such as blood, entrapped in the female member 222 to escape when the male member 224 is inserted into the female member 222.

Referring to FIG. 5, the female member 222 has a female inner diameter (or height, if the female member 222 is not cylindrical) 223 and the male member 224 includes the male face 230 that has an outer diameter (or height, if the male member 224 is not cylindrical) 226. The female member 222 is configured to receive and to provide an interference fit or press fit to the male face 230 of the male member 224.

The female inner diameter 223 can be constant, or it can be sloped or have steps though the inner length of the female member 222 up until a shoulder 228 that prevents the male face 230 of the male member 224 from advancing any further into the female member 222. Thus, the female inner diameter 223 may be larger than an interference fit diameter near a mouth of the female member 222, thereby allowing the male face 230 of the male member 224 to rotate, enter, and exit freely or semi-freely within the female member 222. As the male member 224 is pressed further into the female member 222, the female inner diameter 223 optionally necks down, becoming smaller or narrower, either smoothly or in steps, until an interference fit is achieved. Thus, it will be understood that the female member 222 optionally provides, in part, the ability to adjust the distance 240 (FIG. 4) between bodies 204.

The shoulder 228 optionally narrows or necks down from the female inner diameter 223 to the cannula inner diameter 215, or it can optionally neck down in steps. The shoulder 228 optionally includes a lip or ridge that prevents the male face 230 of the male member 224 from advancing beyond the shoulder 228.

Still referring to FIG. 6, the body or bodies 204, as noted, include an upper bore 206 having a bore inner diameter (or width, if the upper bore 206 is not cylindrical) 207. As noted, the upper bore 206 is fluidly connected to the cannula 214. The upper bore 206 is also fluidly connected to the receptacle 208. The bore inner diameter 207 is less than the receptacle inner diameter (or width, if the receptacle 208 is not cylindrical) 209. Optionally, the bore inner diameter 207 is sufficiently wide to accommodate a K-wire or other guiding mechanism threaded through the screw cannula 164 as discussed above.

The receptacle 208, in addition to the receptacle inner diameter 209 (FIG. 5), has a height 211 and a shoulder, or screw head contact surface 210, as illustrated in FIG. 6. As with the female member 222, the receptacle 208 is configured to receive a head portion 152 of the surgical screw 150 and to provide an interference or press fit between the receptacle 208 and the head portion 152. The receptacle inner diameter 209 can be constant, or it can be sloped or have steps though the inner height 211 of the receptacle 208 up until the screw head contact surface or shoulder 210 that prevents the head portion 152 from advancing any further into the receptacle 208. Thus, the receptacle inner diameter 209 may be larger than an interference fit diameter near a mouth of the receptacle 208, thereby allowing the head portion 152 to rotate, pivot, enter, and exit freely or semi-freely within the receptacle 208. As the head portion 252 is pressed further into the receptacle 208, the receptacle inner diameter 209 optionally necks down, becoming smaller or narrower, either smoothly or in steps, until an interference fit is achieved.

The body 204 and, hence, the receptacle 208 includes a second axis 236. The second axis 236 may align, to a greater or lesser degree with the screw long axis 166 of the surgical screw 150, as is the case for the middle body 204. By align, it is meant that the screw long axis 166 and the second axis 236 will be approximately coincident when the head portion 152 of the surgical screw 150 is inserted into the receptacle 208 of the body 204. As will be discussed in further detail below, it is often not practical and, sometime, even possible, to have the screw long axis 166 and the second axis 236 be coincident due to the tolerances of the manufacturing and surgical placement process, simple variances in the anatomies between patients and other factors. In other circumstances, the screw long axis 166 intersects the second axis 236 of the body at a second angle 237, as illustrated in the left most body 104 of FIG. 3, for which the prior art could not easily accommodate or easily allow.

Referring to FIGS. 7-12, another embodiment of a surgical screw system 300 that includes a plurality of another embodiment of coupling assemblies 302 disclosed herein are illustrated connecting three surgical screws 350 having a threaded portion 362 together.

Figure 7:
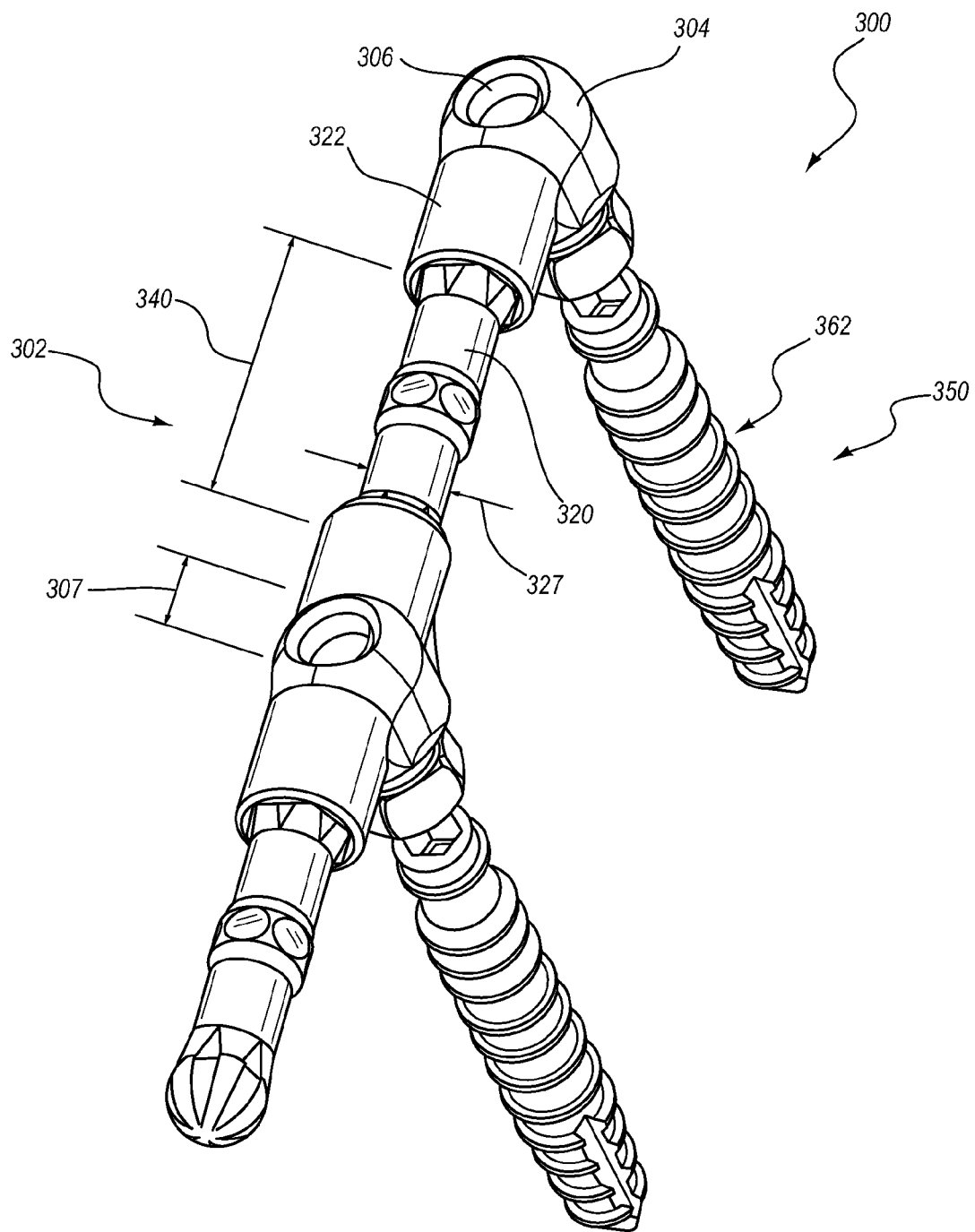
FIG. 7 is another embodiment of a coupling assembly coupled to surgical screws.

The coupling assembly 302 includes at least one body 304; thus, an entire coupling assembly 302 may include a plurality of bodies 304, such as the three bodies 304 illustrated in FIG. 7. The body 304 is illustrated as having a cylindrical shape, although other shapes such as ovoid, spherical, square, and so forth fall within the scope of the disclosure. The body 304 includes an upper bore 306. The body 304 also optionally includes one or more female members 322, one or more male members 324, a combination of female members 322 and male members 324, and, optionally, a coupling rod 320 that includes two or more male members 324 or female members 322. (Illustrated are coupling rods 320 with male members 324, but this is just one embodiment of the coupling rod, as will be understood.) Thus, while FIG. 7 illustrates bodies 304 that have one or two male members 324 and/or female members 322, and one coupling rod 320, one having skill in the art would understand that a body 304 could have 3, 4, or more male members 324 and/or female members 322 and/or coupling rods 320, depending on the intended purpose of the coupling assembly 302.

Figure 9:
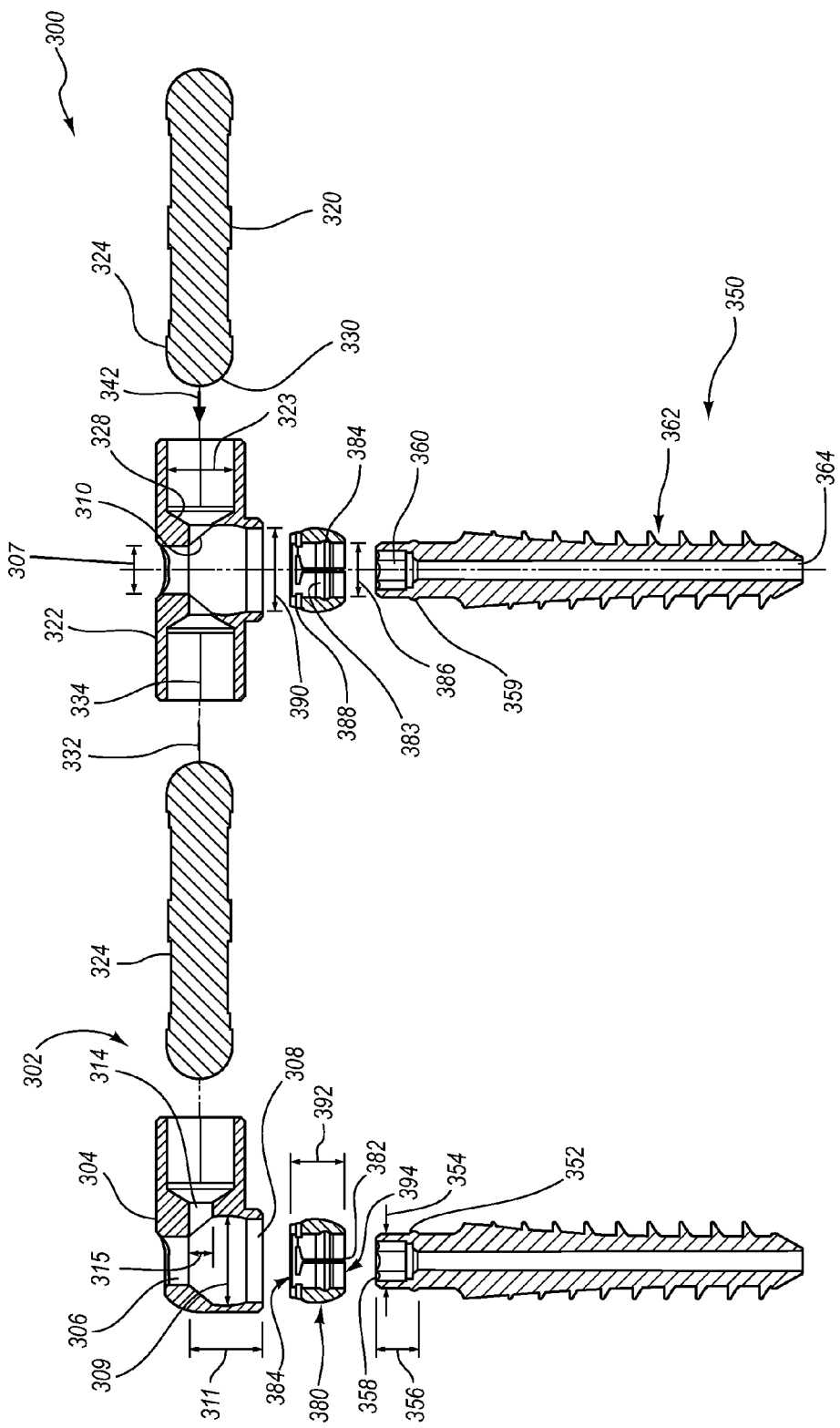
FIG. 9 is a view of cross-section C-C of the embodiment of the exploded view of the coupling assembly shown in FIG. 8.
Figure 10:
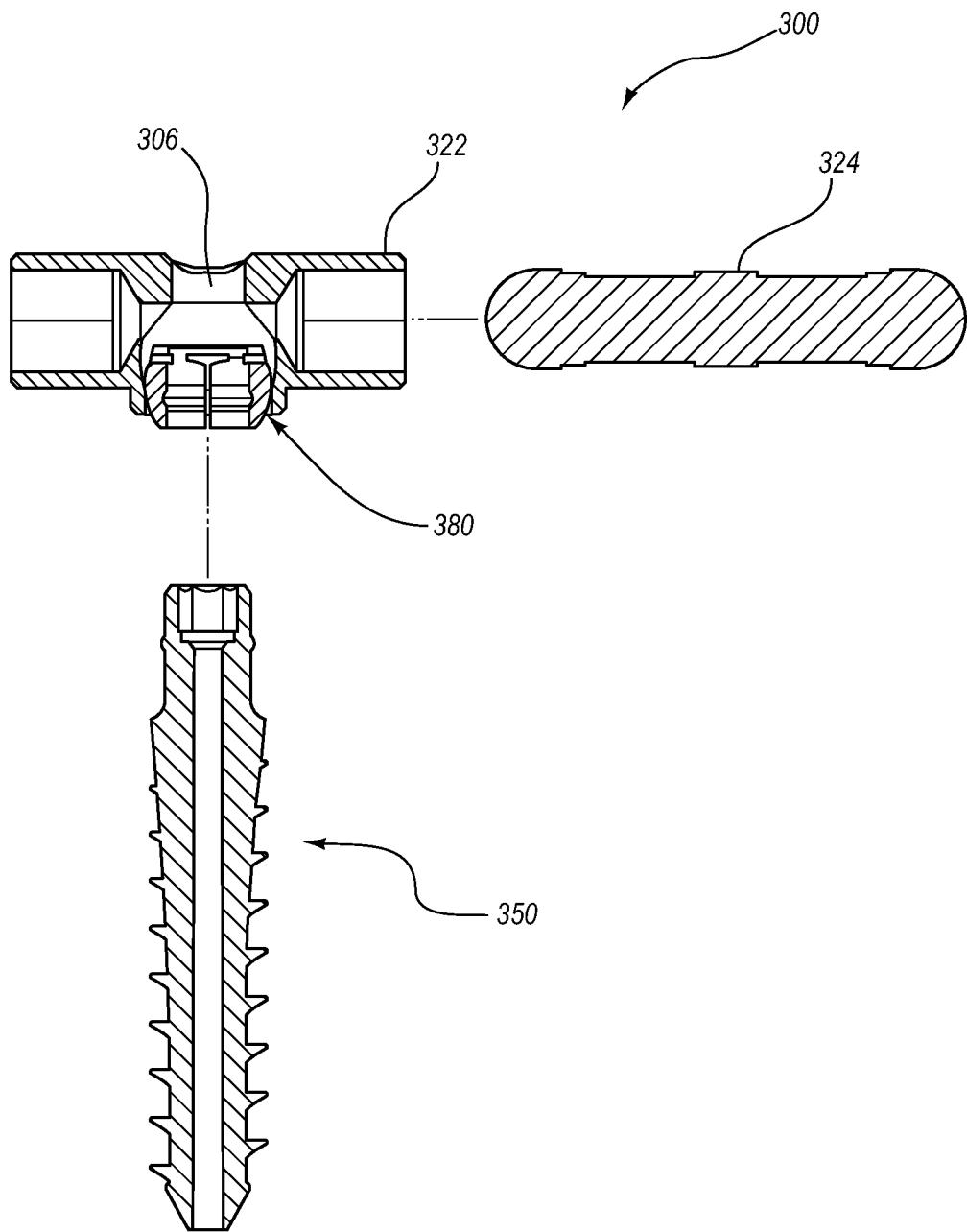
FIG. 10 is a detail view of a partially assembled embodiment of the coupling assembly shown in FIG. 9.

Referring to FIG. 9, the embodiment of the surgical screw system 300 and the coupling assembly 302 of FIG. 7 is shown in exploded view. The surgical screws 350 include a threaded portion 362 configured to engage the bone of a patient as part of an orthopedic surgical procedure. The surgical screws 350 have a head portion 352 that is received by the coupling assembly 302 as will be discussed in further detail below. The head portion 352 has a height 356 and an outer diameter 354. It will be noted, in comparison to the head portion 152 of FIGS. 1-6, the head portion 352 does not have an extended spherical shape to it, although it is optional to have such a shape. The head portion 352 also includes a driving feature 360 for use with various tools to drive the surgical screw 350 into the bone. Illustrated in FIG. 9, the driving feature 160 is an Allen-key or hex-head configuration, although other configurations are known in the art. The surgical screw 350 includes a screw long axis 366 (FIG. 11) and a screw cannula 364, illustrated in the cross-section C-C in FIG. 9. As one having skill in the art would understand, the screw cannula 364 allows the use of a K-wire or other guiding mechanism, as discussed above.

Figure 11:
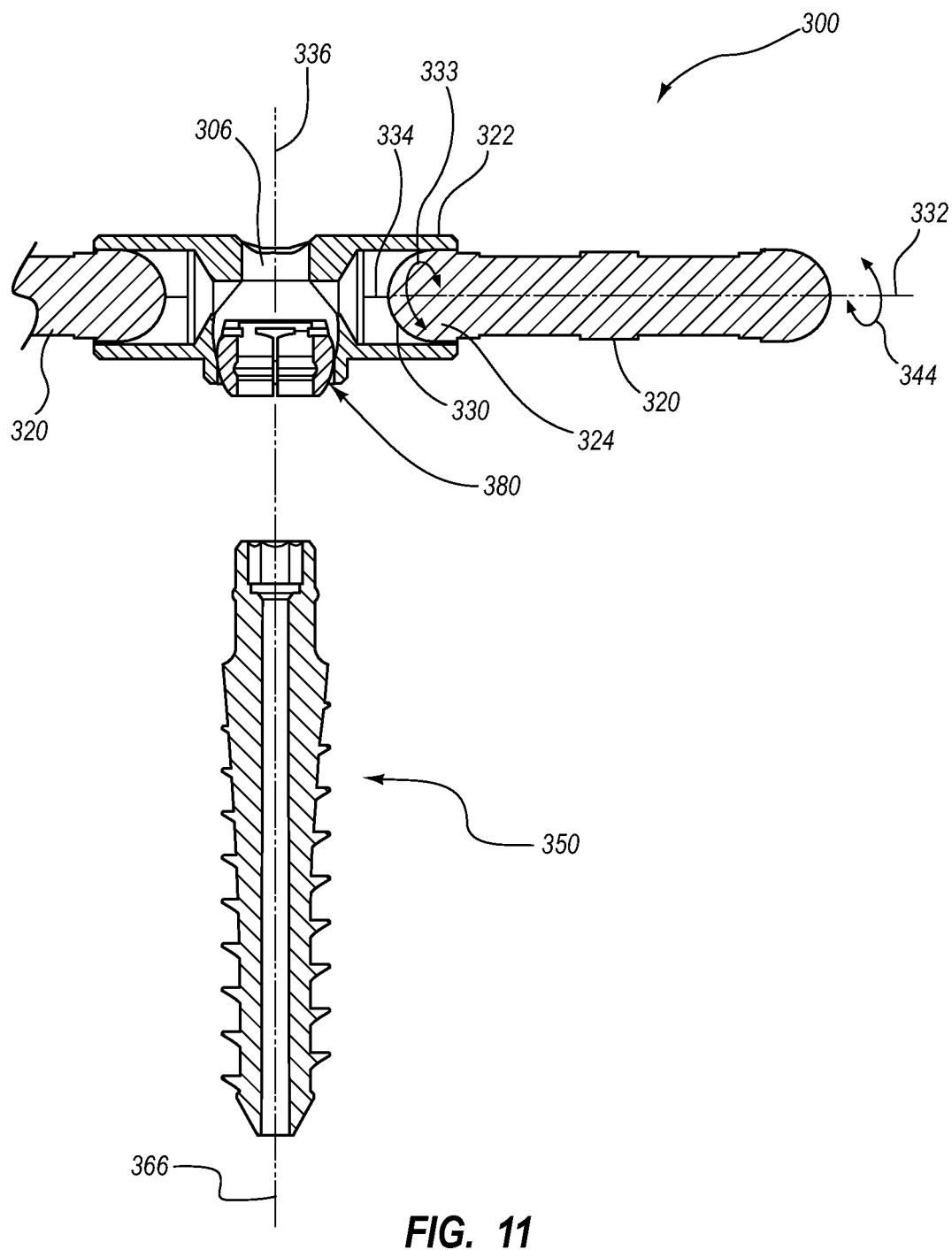
FIG. 11 is another detail view of a partially assembled embodiment of the coupling assembly shown in FIG. 9; and, FIG. 12 is a detail view of an assembled embodiment of the coupling assembly shown in FIG. 9.

Referring to FIGS. 9 and 11, the male member 324 and the coupling rod 320 include a long axis 232 that aligns, to a greater or lesser degree with a first axis 334 of the body 304. By align, it is meant that the long axis 332 and the first axis 334 will be approximately coincident when the male member 324 (whether included with a body 304 or a coupling rod 320) is inserted via a force 342 (FIG. 9) into the female member 322 of the body 304. As will be discussed in further detail below, it is often not practical and, sometime, even possible, to have the long axis 332 and the first axis 334 be coincident due to the tolerances of the manufacturing and surgical placement process, simple variances in the anatomies between patients and other factors. Thus, there often exists a first angle 333 between the intersection of the long axis 332 and the first axis 334, for which the prior art could not easily accommodate or easily allow.

Referring to FIG. 9, the body 304 optionally includes a cannula 314 having a cannula inner diameter (or height, if the cannula is not cylindrical) 315. The cannula 314 is connected to the upper bore 306 and provides a route for any fluids, such as blood, entrapped in the female member 322 to escape when the male member 324 is inserted into the female member 322.

Figure 8:
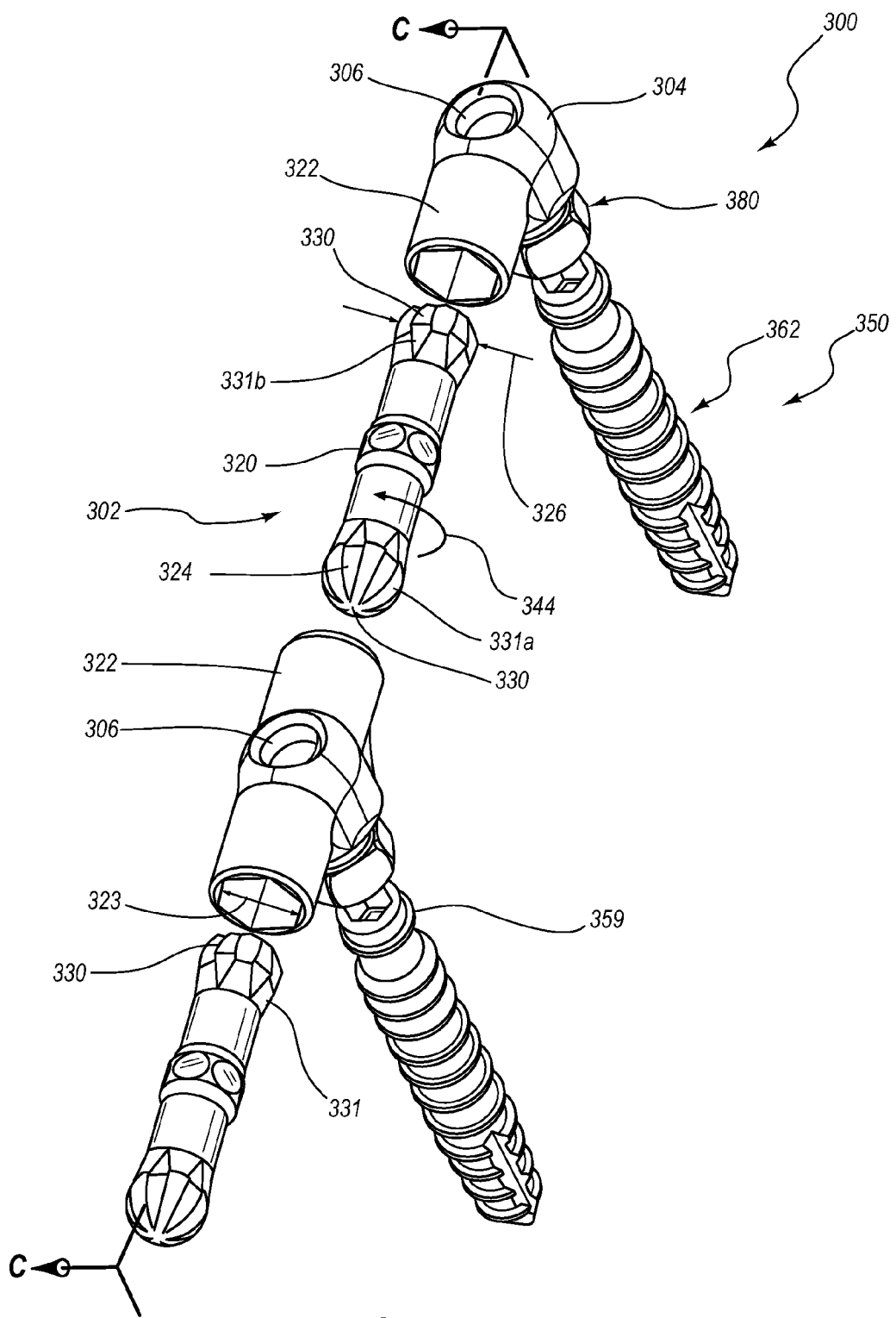
FIG. 8 is an exploded view of the embodiment of the coupling assembly shown in FIG. 7.

Referring to FIG. 8, the female member 322 has a female inner diameter (or height, if the female member 322 is not cylindrical) 323 and the male member 324 includes the male face 330 that has an outer diameter (or height, if the male member 324 is not cylindrical) 326. The female member 322 is configured to receive and to provide an interference fit or press fit to the male face 330 of the male member 324.

Optionally, embodiments of the male face 330 illustrated in FIG. 8 includes a locking mechanism 331, such as a hex head, threads, flutes, ridges, and other similar types of locking mechanisms to engage the female member 322 in a locking arrangement as an alternative to or, optionally, as a supplement to, the interference fit. The locking mechanism 331 optionally can be included on just one or both of the male faces 330 of the coupling rod 320. Optionally, the locking mechanism 331 can be engaged to interface with the female member 322 by rotating the coupling rod 320 and/or the male member 324 in the direction 344 around a long axis 332, as illustrated in FIGS. 9 and 11. Optionally, the locking mechanism 331 on the male faces 330 of the coupling rod 320 can be configured to be the same or different. For example, a first locking mechanism 331a optionally has right hand threads, whereas the locking mechanism 331b optionally has left hand threads. To engage the locking mechanisms 331a and 331b with the female member 322 (and any interference fit between the two), the coupling rod 320 need only be rotated in the direction 344, thereby engaging both locking mechanisms 331a and 331b near simultaneously.

Referring to FIGS. 8 and 9, the female inner diameter 323 can be constant, or it can be sloped or have steps though the inner length of the female member 322 up until a shoulder 328 that prevents the male face 330 of the male member 324 from advancing any further into the female member 322. Thus, the female inner diameter 323 may be larger than an interference fit diameter near a mouth of the female member 322, thereby allowing the male face 330 of the male member 324 to rotate, enter, and exit freely or semi-freely within the female member 322 before engaging any locking mechanism 331. As the male member 324 is pressed further into the female member 322, the female inner diameter 323 optionally necks down, becoming smaller or narrower, either smoothly or in steps, until an interference fit is achieved and/or the locking mechanism 331 is engaged. Thus, it will be understood that the female member 322 optionally provides, in part, the ability to adjust the distance 340 (FIG. 7) between bodies 304.

The shoulder 328 optionally narrows or necks down from the female inner diameter 323 to the cannula inner diameter 315, or it can optionally neck down in steps. The shoulder 328 optionally includes a lip or ridge that prevents the male face 330 of the male member 324 from advancing beyond the shoulder 328.

Still referring to FIG. 9, the body or bodies 304, as noted, include an upper bore 306 having a bore inner diameter (or width, if the upper bore 306 is not cylindrical) 307. As noted, the upper bore 306 is fluidly connected to the cannula 314. The upper bore 306 is also fluidly connected to the receptacle 308. The bore inner diameter 307 is less than the receptacle inner diameter (or width, if the receptacle 308 is not cylindrical) 309. Optionally, the bore inner diameter 307 is sufficiently wide to accommodate a K-wire or other guiding mechanism threaded through the screw cannula 364 as discussed above.

The receptacle 308, in addition to the receptacle inner diameter 309 (FIG. 9), has a height 311 and a shoulder, or contact surface 310, as illustrated in FIG. 6. As with the female member 322, the receptacle 308 is optionally configured to receive a head portion 352 of the surgical screw 350 and to provide an interference or press fit between the receptacle 308 and the head portion 352. The receptacle inner diameter 309 can be constant, or it can be sloped or have steps though the inner height 311 of the receptacle 308 up until the contact surface or shoulder 310 that prevents the head portion 352 from advancing any further into the receptacle 308. Thus, the receptacle inner diameter 309 may be larger than an interference fit diameter near a mouth of the receptacle 308, thereby allowing the head portion 352 to rotate, enter, and exit freely or semi-freely within the receptacle 308. As the head portion 352 is pressed further into the receptacle 308, the receptacle inner diameter 309 optionally necks down, becoming smaller or narrower, either smoothly or in steps, until an interference fit is achieved.

Alternatively, and as illustrated in FIG. 9, the receptacle 308 can be configured to receive a split-ring 380. The split ring 380 includes a plurality of fingers 383 separated by slots 382. The split-ring 380 has a height 392, an split-ring outer diameter 390, a recess 394 having a recess inner diameter 386, and an optional flat top 390. The split-ring 80 is configured to receive the head portion 352 of the surgical screw 350 within the recess 394. The fingers 383 elastically deform, such as with a spring-like manner, to engage and grasp the head portion 352 of the surgical screw 350. Optionally, the recess 394 includes a channel or slot 384 configured to engage a lip or ridge 359 on the head portion 352 of the surgical screw 350 to better secure the head portion 352 within the recess 394 of the split-ring 380. A benefit of the split ring 380 is that it elastically, and thus easily, engages and disengages from the head portion 352 of a surgical screw 350 that has been implanted in a bone, thus more easily allowing for adjustment of the body 304 and, therefore, the coupling assembly 302, during a procedure.

The split-ring 380 may be partially received within the receptacle 308 initially (FIGS. 10 and 11) or it may engage the head portion 352 of the surgical screw 350 prior to being received by the receptacle 308 (not shown). Regardless, once properly adjusted and positioned, the receptacle 308 receives the split ring 380 therein with an interference fit as illustrated in FIG. 12 and as described above vis-à-vis the embodiments in which the receptacle 108, 208, 308 directly engage a head portion 152, 352 of the surgical screw 150, 350.

Figure 12:
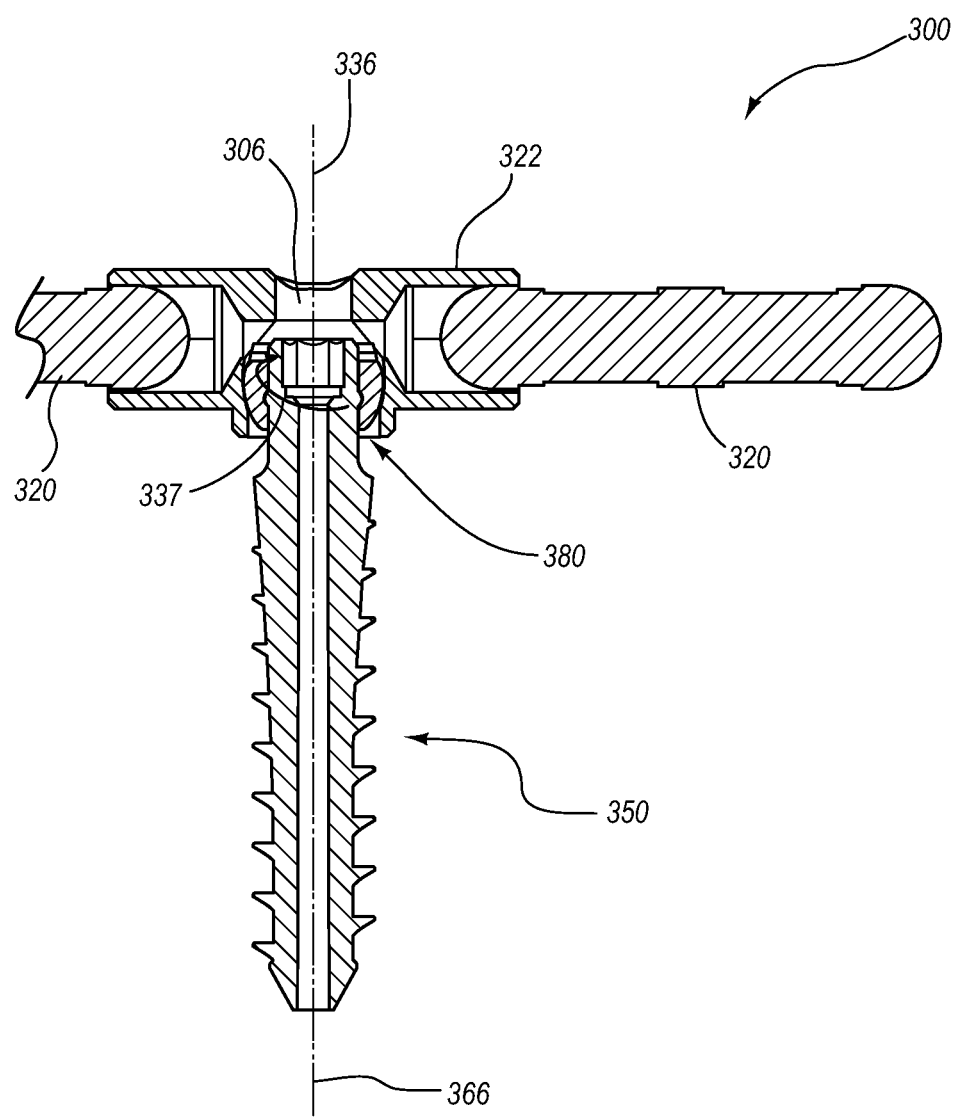

Referring to FIGS. 11 and 12, the body 304 and, hence, the receptacle 308 includes a second axis 336. The second axis 336 may align, to a greater or lesser degree with the screw long axis 366 of the surgical screw 352. By align, it is meant that the screw long axis 366 and the second axis 336 will be approximately coincident when the head portion 352 of the surgical screw 350 is inserted into the receptacle 308 of the body 304. As will be discussed in further detail below, it is often not practical and, sometime, even possible, to have the screw long axis 366 and the second axis 336 be coincident due to the tolerances of the manufacturing and surgical placement process, simple variances in the anatomies between patients and other factors. In other circumstances, the screw long axis 366 intersects the second axis 336 of the body at a second angle 337, as illustrated in FIG. 12, for which the prior art could not easily accommodate or easily allow.

Methods of making and using embodiments of the coupling assemblies disclosed herein are also disclosed.

For example, and as mentioned, embodiments of coupling assemblies disclosed herein are suitable for surgical orthopedic procedures, such as stabilize fractures, the spine, and other similar procedures. In such instances, a surgeon typically, although not necessarily, implanted one or more surgical screws into a bone of a patient, often with the aid of a K-wire or other guiding mechanism. It is typically desirable to couple that first surgical screw to another surgical screw with a coupling assembly to provide stability, rigidity, and, optionally, a platform for other devices, such as fusion rods, plates, and the like.

As noted, surgeons were required to have available coupling assemblies and their components in many different lengths and shapes to accommodate various factors, including manufacturing tolerances, a patient's particular anatomy and injury that would require placement of the surgical screws in a potentially infinite variety of locations, and slight variation from a desired location of the surgical screw that may occur during the procedure.

Furthermore, prior art devices typically required locking screws, nuts, crimping tools, and other similar devices to effect a fixed connection between the coupling assembly and the surgical screw. Rigid rods with inflexible connections and/or through-holes into which the rods were positioned, as disclosed in prior art devices, could not easily accommodate the various factors discussed above and, at times, a surgeon would have to bend the rod. Thus, the prior art devices had a larger profile, typically resulting in more pain to the patient and required more parts, thereby increasing the complexity of the process and increasing the risk that a component might be misplaced or lost.

Embodiments of the coupling assemblies disclosed herein, however, have fewer parts, accommodate a variety of tolerances, angles, and other factors that occur during any surgical procedure, allow for adjustment during the procedure, and other benefits as discussed above and will be discussed here. While reference will be made to the embodiments disclosed above in reference to FIGS. 7-12, it will be understood by one of skill in the art that embodiments of these methods and variations thereof apply to each of the embodiments disclosed herein.

Embodiments of the methods of implanting a coupling assembly 302, therefore, include obtaining a first body 304 and a second body 304, each body 304 including an upper bore 302 and a receptacle 308 configured to receive a head portion 352 of a surgical screw 350 that has been implanted in a patient. The receptacle 308, as noted provides an interference fit with the head portion 352 and, optionally, a split-ring 380, as described above. The body 304 also includes at least one of a male member 324, female member 322, and, optionally, a coupling rod 320 that includes a male member 324. The receptacle 308 is positioned on the head portion 352 and/or a split-ring 380 so that the body 304 can move relative to the head portion 352. The male member 324, whether as part of a body 304 or a coupling rod 320, is positioned within the female member 322 so that the body 304 and the female member 322 can move relative to the male member 324, which can reduce the likelihood that a rigid rod would have to be bent to accommodate a fixed coupling system. Thus, the coupling assembly 302 can be assembled and disassembled easily, perhaps many times, before the interference fit is engaged. Likewise, the coupling assembly 302 can be assembled in-situ or before hand—a step eased by the flexibility and adaptability provided by the disclosed embodiments—providing further ease of use compared to prior art devices. The interference fit of the female member 322 and the receptacle 308 is then engaged (in either order or simultaneously) with the male member 324 and the head portion 352, respectively.

As the interference fit is not necessarily immediately engaged, the angle between the first axis 334 and the long axis 332, as well as the second axis 336 and the screw long axis 337 can be adjusted and accommodated for misalignment and for the various factors noted above. Similarly, the distance 340 between bodies can be adjusted by adjusted the depth to which the male member 324 is inserted into the female member 322, thereby accommodating for the various factors noted above. Furthermore, the relative height of the body 304 above the head portion 352 can be adjusted by adjusted the depth to which the head portion 352 (or split-ring 380) is inserted into the receptacle 308, thereby accommodating a higher or lower profile as desired and thereby providing a lower profile assembly than prior art devices that use set screws and the like. Should the male member 324 include a male face 330 with a locking mechanism 331, the locking mechanism can be engaged as disclosed above.

Methods of making embodiments of the coupling assemblies are also disclosed. These methods include forming a first body 308 that includes an upper bore 308, a receptacle 308, at least one of a male member 324, a female member 322, and, optionally, a coupling rod 320. The female member 322 is configured to receive the male member 324. Optionally, the male member 324 is configured to have a male face 330 that includes a locking mechanism 331 as described above. Optionally, the receptacle 308 is formed and configured to receive a head portion 352 of a surgical screw 350 and/or a split-ring 380 that, in turn, is formed and configured to receive a head portion 352 of the surgical screw 350.

The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A coupling assembly comprising:
  a first body and a second body, each of said first body and said second body including:
    an upper bore; and
    a receptacle configured to receive a head portion of a surgical screw and to provide an interference fit with said head portion without the use of a fastener, said receptacle connected to said upper bore; and
  one of the first and second bodies including a male member comprising a spherical face and another of the first and second bodies including a female member, said female member having a cylindrical receptacle and being configured to receive said male member and to provide an interference fit with said male member in said cylindrical receptacle without the use of a fastener such that said male member is prevented from freely moving within said female member, said female member and said male member thereby configured to couple said first body and said second body together.

2. The coupling assembly of claim 1, wherein said spherical face is configured to accommodate misalignment between a first axis of said body and a long axis of said male member.

3. The coupling assembly of claim 1, further comprising a cannula connecting said female member to said upper bore.

4. The coupling assembly of claim 1, wherein said male member and said female member are configured to permit adjustment of a distance between said first body and said second body.

5. The coupling assembly of claim 1, wherein said receptacle is configured to accommodate misalignment between a second axis of said body and a long axis of said surgical screw.

6. A coupling assembly comprising: a first body, said first body including:
  an upper bore;
  a receptacle configured to receive a head portion of a surgical screw and to provide an interference fit with said head portion, said receptacle connected to said upper bore; and,
  at least one of:
    a male member comprising a spherical face that is monolithic with the male member, the male member being configured to be received by a cylindrical receptacle of a female member of another coupling assembly and to provide an interference fit with said cylindrical receptacle of said female member; or
    another cylindrical receptacle of another female member, said another cylindrical receptacle of said another female member configured to receive another male member comprising a spherical face that is monolithic with the male member, the male member being of another coupling assembly, and to provide an interference fit with said another male member within said cylindrical receptacle; wherein
  each interference fit results in the interference fit components being unable to freely rotate, pivot, enter and exit relative to one another.

7. The coupling assembly of claim 6, wherein said spherical face is configured to accommodate misalignment between a first axis of said first body and a long axis of said male member.

8. The coupling assembly of claim 6, further comprising a cannula connecting said female member to said upper bore.

9. The coupling assembly of claim 6, wherein said male member or said female member is configured to permit adjustment of a distance between said first body and said another coupling assembly body.

10. The coupling assembly of claim 6, wherein said receptacle is configured to accommodate misalignment between a second axis of said first body and a long axis of said surgical screw.

* * * * *